(12) United States Patent
Goutopoulos et al.

(10) Patent No.: US 8,889,719 B2
(45) Date of Patent: Nov. 18, 2014

(54) PHENYLAMINO ISONICOTINAMIDE COMPOUNDS

(71) Applicants: Andreas Goutopoulos, Boston, MA (US); Henry Yu, Wellesley, MA (US); Benny C. Askew, Jr., Marshfield, MA (US); Lesley Liu-Bujalski, Bedford, MA (US)

(72) Inventors: Andreas Goutopoulos, Boston, MA (US); Henry Yu, Wellesley, MA (US); Benny C. Askew, Jr., Marshfield, MA (US); Lesley Liu-Bujalski, Bedford, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/785,120

(22) Filed: Mar. 5, 2013

(65) Prior Publication Data

US 2013/0184314 A1   Jul. 18, 2013

Related U.S. Application Data

(62) Division of application No. 13/057,052, filed as application No. PCT/US2009/051817 on Jul. 27, 2009, now Pat. No. 8,404,725.

(60) Provisional application No. 61/137,858, filed on Aug. 4, 2008.

(51) Int. Cl.
  *A61K 31/455*  (2006.01)
  *C07D 213/46*  (2006.01)
  *C07D 213/82*  (2006.01)
  *C07D 213/79*  (2006.01)
  *C07D 213/81*  (2006.01)

(52) U.S. Cl.
  CPC ............ *C07D 213/82* (2013.01); *C07D 213/79* (2013.01); *C07D 213/81* (2013.01)
  USPC ............ 514/352; 546/310; 546/314; 546/315

(58) Field of Classification Search
  USPC .......................... 546/310, 314, 315; 514/352
  See application file for complete search history.

(56) References Cited

U.S. PATENT DOCUMENTS 7,956,191 B2 * 6/2011 Abel et al. .................... 546/310

* cited by examiner

*Primary Examiner* — Kamal Saeed
*Assistant Examiner* — Janet L Coppins

(57) ABSTRACT

The invention provides novel compounds according to Formula (I), their manufacture and use for the treatment of hyperproliferative diseases, such as cancer, restenosis and inflammation.

14 Claims, No Drawings

PHENYLAMINO ISONICOTINAMIDE COMPOUNDS

FIELD OF THE INVENTION

The invention relates to a series of substituted phenylamino isonicotinamide compounds that are useful in the treatment of hyperproliferative diseases, such as cancer and inflammatory disorders, in mammals. Also disclosed is the use of such compounds in the treatment of hyperproliferative diseases in mammals, especially humans, and pharmaceutical compositions containing such compounds.

SUMMARY OF THE RELATED ART

The Ras/Raf/MEK/ERK pathway is a central signal transduction pathway, which transmits signals from multiple cell surface receptors to transcription factors in the nucleus which regulate gene expression. This pathway is frequently referred to as the MAP kinase pathway as MAPK stands for mitogen-activated protein kinase indicating that this pathway can be stimulated by mitogens, cytokines and growth factors (Steelman et al., Leukemia 2004, 18, 189-218). Depending upon the stimulus and cell type, this pathway can transmit signals, which result in the prevention or induction of apoptosis or cell cycle progression. The Ras/Raf/MEK/ERK pathway has been shown to play important roles in cell proliferation and the prevention of apoptosis. Aberrant activation of this pathway is commonly observed in malignantly transformed cells. Amplification of ras proto-oncogenes and activating mutations that lead to the expression of constitutively active Ras proteins are observed in approximately 30% of all human cancers (Stirewalt et al., Blood 2001, 97, 3589-95). Mutated, oncogenic forms of Ras are found in 50% of colon and >90% pancreatic cancers as well as many other types of cancers (Kohl et al., Science 1993, 260, 1834-1837). The effects of Ras on proliferation and tumorigenesis have been documented in immortal cell lines (McCubrey et al., Int J Oncol 1995, 7, 295 310). bRaf mutations have been identified in more than 60% of malignant melanoma (Davies, H et al., Nature 2002, 417, 949-954). Given the high level of mutations that have been detected in Ras, this pathway has always been considered a key target for therapeutic intervention (Chang et al., Leukemia 2003, 17, 1263-93).

The Ras/Raf/MEK/ERK signaling pathway can regulate proliferation through downstream transcription factor targets including NF-$\kappa^{\kappa}$B, CREB, Ets-1, AP-1 and c-Myc. ERKs can directly phosphorylate Ets-1, AP-1 and c-Myc, which lead to their activation. Alternatively, ERKs can phosphorylate and activate the downstream kinase target RSK, which then phosphorylates and activates transcription factors, such as CREB. These transcription factors induce the expression of genes important for cell cycle progression, for example, Cdk's, cyclins, growth factors, and for apoptosis prevention, for example, antiapoptotic Bcl-2 and cytokines. Overall, treatment of cells with growth factors leads to the activation of ERKs which results in proliferation and, in some cases, differentiation (Lewis et al., Adv. Cancer Res, 1998, 74, 49-139). The MEK family of genes consists of five genes: MEK1, MEK2, MEK3, MEK4 and MEK5. This family of dual-specificity kinases has both serine/threonine and tyrosine kinase activity. The structure of MEK consists of an amino-terminal negative regulatory domain and a carboxy-terminal MAP kinase-binding domain, which is necessary for binding and activation of ERKs. Deletion of the regulatory MEK1 domain results in constitutive MEK1 and ERK activation (Steelman et al., Leukemia 2004, 18, 189-218).

MEK1 is a 393-amino-acid protein with a molecular weight of 44 kDa (Crews et al., Science 1992, 258, 478-80). MEK1 is modestly expressed in embryonic development and is elevated in adult tissue with the highest levels detected in brain tissue. MEK1 requires phosphorylation of S218 and S222 for activation, and substitution of these residues with either aspartic acid (D) or glutamic acid (E) led to an increase in activity and foci formation in NIH3T3 cells (Huang et al., Mol Biol Cell, 1995, 6, 237-45). Constitutive activity of MEK1 in primary cell culture promotes senescence and induces p53 and p16$^{INK4a}$, and the opposite was observed in immortalized cells or cells lacking either p53 or p16$^{INK4a}$ (Lin et al., Genes Dev, 1998, 12, 3008-3019). Constitutive activity of MEK1 inhibits NF-$\kappa^{\kappa}$B transcription by negatively regulating p38 MAPK activity (Carter et al., J Biol Chem 2000, 275, 27858-64). The main physiological substrates of MEK are the members of the ERK (extracellular signal-regulated kinase) or MAPK (mitogen activated protein kinase) family of proteins. Aberrant expression of MEK1 has been detected in many different types of cancer, and mutated forms of MEK1 will transform fibroblast, hematopoietic and other cell types.

Constitutive activation of MEK1 results in cellular transformation. MEK1 therefore represents a likely target for pharmacological intervention in proliferative and inflammatory diseases (Lee et al., Nature 1994, 372, 739-746; Dudley et al., Proc. Natl. Acad. Sci. U.S.A. 1995, 92, 7686-7689).

Useful inhibitors of MEK have been developed that show potential therapeutic benefit in several studies. For example, small molecule MEK inhibitors have been shown to inhibit human tumor growth in nude mouse xenografts (Yeh, T. et al, Proceedings of the American Association of Cancer Research 2004, 45, Abs 3889 and Lee, P. et al., Proceedings of the American Association of Cancer Research 2004, 45, Abs 3890). MEK inhibitors also entered clinical trials, i.e. ARRY142886 (Wallace, E. et al, Proceedings of the American Association of Cancer Research 2004, 45, Abs 3891; Adjei, A. A. et al, Journal of Clinical Oncology 2008, 26, 2139-2146; Shannon, A. M. et al, Molecular Cancer Therapeutics 2007, 6, 3414S-3415S Part 2), PD-0325901 (Swanton C, Johnston S IDDB MEETING REPORT 2003, February 13-1; Haura, E. B. et al, Molecular Cancer Therapeutics 2007, 6, 3468S-3469S Part 2; LoRusso, P. A. et al, Molecular Cancer Therapeutics 2007, 6, 3469S-3470S Part 2), PD-184352 (Waterhouse et al., Proceedings of the American Society for Clinical Oncology 2003, 22, Abs 816), XL-518 (Johnston, S., Molecular Cancer Therapeutics 2007, 6, 3595S-3595S Part 2), RDEA-119 (2007 press release), and RDEA-436 (2008 press release). Compounds suitable as MEK inhibitors are also disclosed in U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077855; WO03/077914; WO2004/005284; WO2004/056789, WO2006/045514, WO2008/076415, WO2007/121269, and WO2007/121481.

DESCRIPTION OF THE INVENTION

It is the object of the present invention to provide novel MEK inhibitors useful in the treatment of hyperproliferative diseases related to the hyperactivity of MEK as well as diseases modulated by the MEK cascade, such as cancer and inflammation in mammals with superior pharmacological properties both with respect to their activities as well as their solubility, metabolic clearance and bioavailability characteristics.

As a result, this invention provides novel, substituted phenylamino isonicotinamide compounds and pharmaceutically acceptable salts, solvates or prodrugs thereof, that are MEK inhibitors and useful in the treatment of the above mentioned diseases. The compounds are defined by Formula (I):

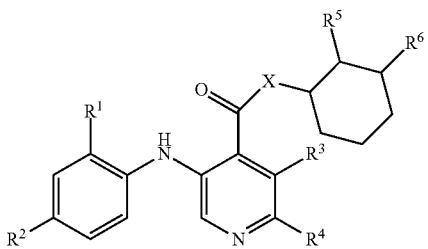

Formula (I)

and pharmaceutically acceptable salts, solvates or prodrugs thereof,
wherein:
X is NH or O,
$R^1$ is hydrogen, methyl, ethyl, n-propyl, i-propyl, SH or Hal,
$R^2$ is hydrogen, methoxy, ethoxy, acetylene, cyano, SH or Hal,
$R^3$, $R^4$ are independently selected from hydrogen, SH or Hal,
$R^5$, $R^6$ are independently selected from OH, SH or $NH_2$ and
Hal is F, Cl, Br or I.

Preferred are compounds of Subformulae IA, IB, IC, ID, IE, IF, IG and IH of Formula (I), and pharmaceutically acceptable salts, solvates or prodrugs thereof, wherein in Subformula IA
X is NH,
$R^1$ is Hal, methyl or ethyl,
$R^2$ is hydrogen, Hal, methoxy or acetylene,
$R^3$ is hydrogen or Hal,
$R^4$ is hydrogen or Hal,
$R^5$, $R^6$ are OH,
Hal is F, Cl, Br or I,
in Subformula IB
X is NH,
$R^1$ is Hal,
$R^2$ is hydrogen or Hal,
$R^3$ is hydrogen or Hal,
$R^4$ is hydrogen or Hal,
$R^5$, $R^6$ are OH,
Hal is F, Cl, Br or I,
in Subformula IC
X is NH,
$R^1$ is F, Cl, methyl or ethyl,
$R^2$ is hydrogen, I, Br, methoxy or acetylene,
$R^3$ is hydrogen or Hal,
$R^4$ is hydrogen or Hal,
$R^5$, $R^6$ are OH,
Hal is F, Cl, Br or I,
in Subformula ID
X is NH,
$R^1$ is F, Cl, methyl or ethyl,
$R^2$ is hydrogen, I, Br, methoxy or acetylene,
$R^3$ is hydrogen or F,
$R^4$ is hydrogen or Cl,
$R^5$, $R^6$ are OH,
in Subformula IE
X is NH,
$R^1$ is F or Cl,
$R^2$ is I or Br,
$R^3$ is hydrogen or F,
$R^4$ is hydrogen or Cl,
$R^5$, $R^6$ are OH,
in Subformula IF
X is NH,
$R^1$ is F or Cl,
$R^2$ is I or Br,
$R^3$ is hydrogen or F,
$R^4$ is hydrogen or Cl,
$R^5$, $R^6$ are OH,
in Subformula IG
X is NH,
$R^1$ is F or Cl,
$R^2$ is I or Br,
$R^3$ is hydrogen,
$R^4$ is hydrogen,
$R^5$, $R^6$ are OH,
and in Subformula IH
X is NH,
$R^1$ is F,
$R^2$ is I,
$R^3$ is hydrogen or F,
$R^4$ is hydrogen or Cl,
$R^5$, $R^6$ are OH.

A more preferred group of compounds of Formula (I) and its Subformulae IA, IB, IC, ID, IE, IF, IG and IH corresponds to Formula (II):

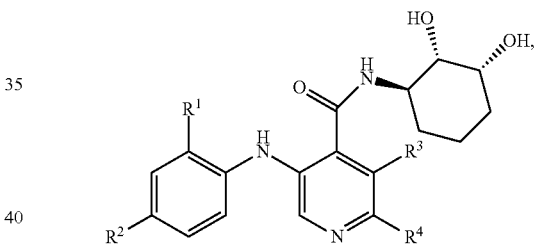

II in which $R^1$, $R^2$, $R^3$, and $R^4$ have the meaning indicated for Formula (I) or its preferred Subformulae IA, IB, IC, ID, IE, IF, IG or IH.

Especially preferred compounds according to Formula (I) and/or Formula (II) include those of the group consisting of

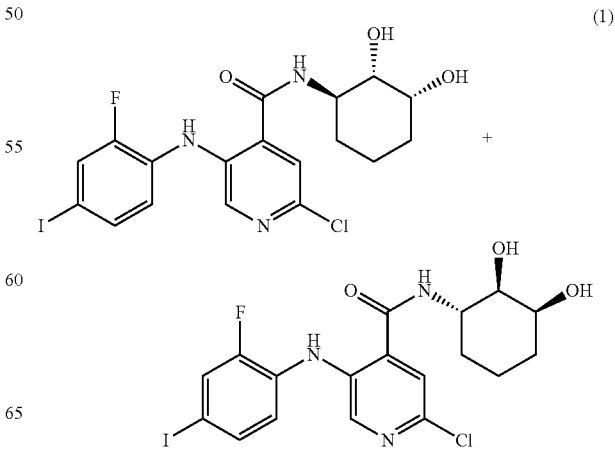

(1)

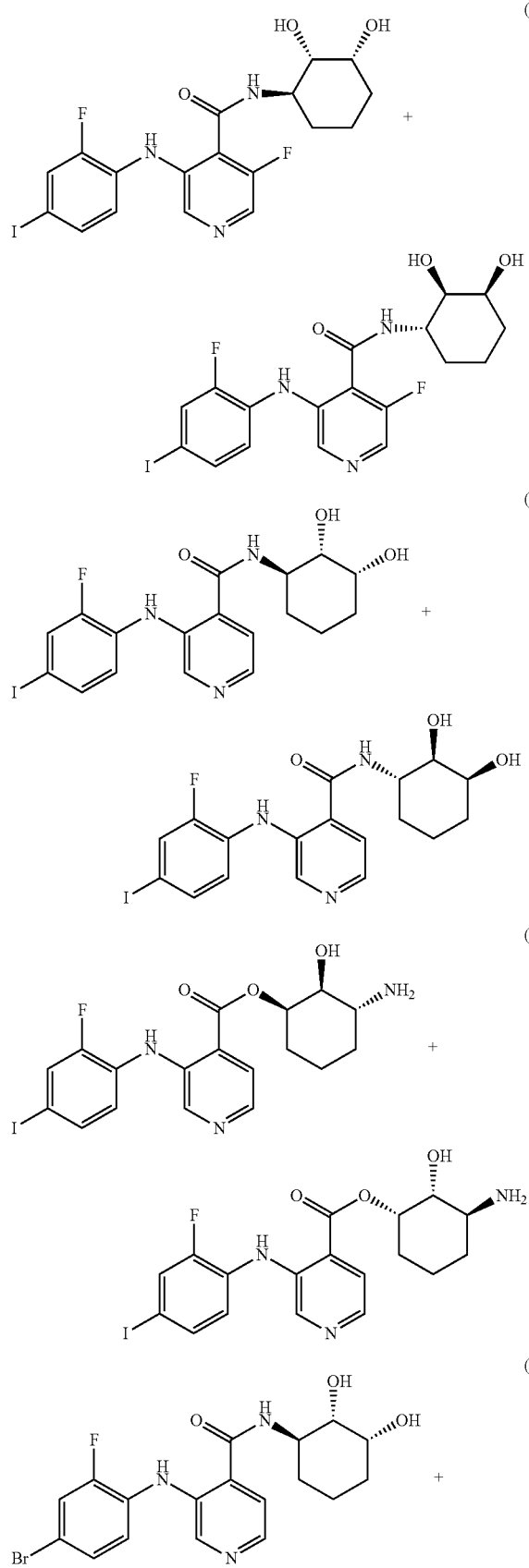
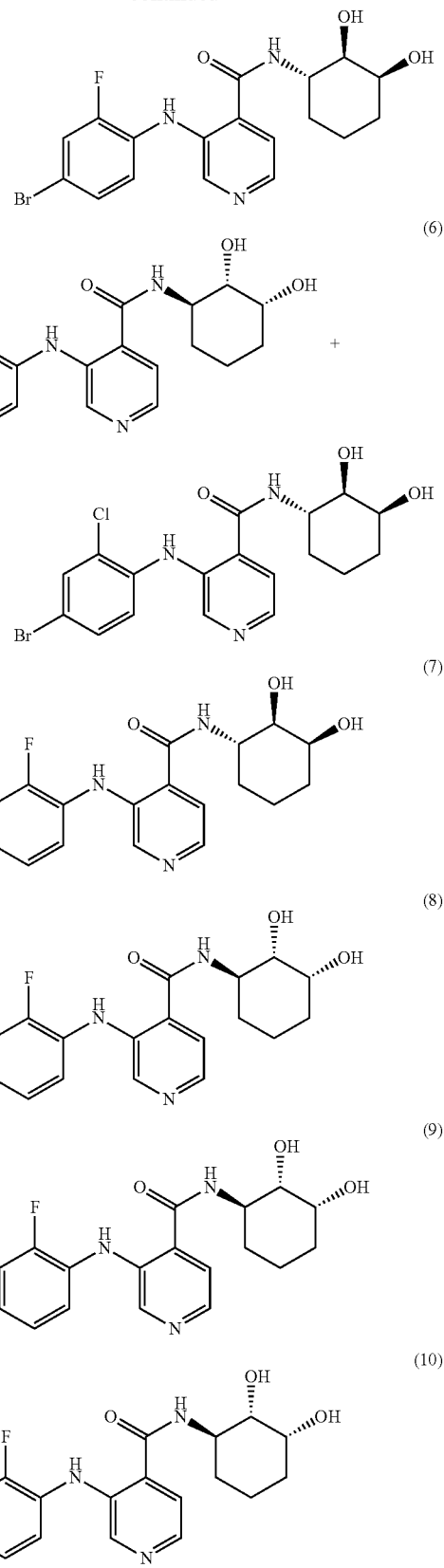
or their pharmaceutically acceptable salts, solvates or prodrugs.

Where two structures are shown with a "+" sign in between, a 1:1 racemic mixture of the two enantiomers is indicated.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other MEK inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, squamous cell, bladder, gastric, pancreatic, breast, head, neck, renal, kidney, ovarian, prostate, colorectal, oesophageal, testicular, gynecological, thyroid cancer, melanoma, hematologic malignancies such as acute myelogenous leukemia, multiple myeloma, chronic myelogneous leukemia, myeloid cell leukemia, or any other type of solid or liquid tumors. In another embodiment, said pharmaceutical composition is for the treatment of a noncancerous hyperproliferative disorder such as benign hyperplasia of the skin (e.g., psoriasis), restenosis, polycystic kidney disease, or prostate (e.g., benign prostatic hypertrophy (BPH)) and also for the treatment of inflammatory and autoimmune diseases such as rheumatoid arthritis, Crohn's disease, asthma, ulcerative colitis, irritable bowel syndrome, multiple sclerosis, lupus erythematosus and others. In another embodiment, said pharmaceutical composition is for the treatment of genetic conditions characterized by upregulation of the MEK/ERK pathway such as the Costello syndrome, Noonan syndrome, cardiofaciocutaneous syndrome and others.

The invention also relates to the use of compounds according to the invention for the preparation of a medicament for the treatment of hyperproliferative diseases related to the hyperactivity of MEK as well as diseases modulated by the MEK cascade in mammals, or disorders mediated by aberrant proliferation, such as cancer and inflammation.

The invention also relates to a compound or pharmaceutical composition for the treatment of pancreatitis or kidney disease (including proliferative glomerulonephritis and diabetes induced renal disease) or pain in a mammal which comprises a therapeutically effective amount of a compound of the present invention, or a pharmaceutically acceptable salt, prodrug or hydrate thereof, and a pharmaceutically acceptable carrier.

The invention also relates to a compound or pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier. The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a use for treating a hyperproliferative disorder in a mammal that comprises administering to said mammal a therapeutically effective amount of a compound of the present invention, or a pharmaceutically acceptable salt, prodrug or hydrate thereof. In one embodiment, said use relates to the treatment of cancer such as brain, lung, squamous cell, bladder, gastric, pancreatic, breast, head, neck, renal, kidney, ovarian, prostate, colorectal, oesophageal, testicular, gynecological or thyroid cancer. In another embodiment, said use relates to the treatment of a non-cancerous hyperproliferative disorders such as benign hyperplasia of the skin (e.g., psoriasis), restenosis, or prostate (e.g., BPH).

The invention also relates to a use for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, antimetabolites, intercalating antibiotics, growth factor inhibitors, antiangiogenic agents, cell cycle inhibitors, enzyme inhibitors, topoisomerase inhibitors, biological response modifiers, antihormones, angiogenesis inhibitors, and anti-androgens, or immune modulators.

The invention also relates to a use for treating pancreatitis or kidney disease or pain in a mammal that comprises administering to said mammal a therapeutically effective amount of a compound of the present invention, or a pharmaceutically acceptable salt, prodrug or hydrate thereof. The invention also relates to a use for preventing blastocyte implantation in a mammal that comprises administering to said mammal a therapeutically effective amount of a compound of the present invention, or a pharmaceutically acceptable salt, prodrug or hydrate thereof.

The invention also relates to a use for treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer. Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, chronic myelomonocytic leukemias, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of a) an effective amount of a compound according to the invention or a physiologically acceptable salt, solvate or prodrug thereof, and b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Some abbreviations that may appear in this application are as follows:

ABBREVIATIONS

| Designation | |
|---|---|
| Ac | Acetyl |
| ACN | acetonitrile |
| b | Broad peak |
| BSA | Bovine serum albumin |
| CDI | N,N-Carbonyldiimidazole |
| d | Doublet |
| DBU | 1,8-diazabicyclo[5.4.0]undec-7-ene |
| DCM | Dichloromethane |
| dd | Doublet of doublets |
| DIPEA | N-Ethyldiisopropylamine |
| DMEM | Dulbecco's Modified Eagle's Medium |
| DMF | N,N-Dimethylformamide |
| DMSO | dimethylsulfoxide |
| DTT | dithiothreitol |
| EDCI | 1-(3-Dimethylaminopropyl)-3-ethylcarbodiimide hydrochloride |
| EDTA | Ethylenediaminetetraacetic acid |
| Et | ethyl |
| h | hour |
| HOBt | 1-hydroxybenzotriazole |
| HPLC | High pressure liquid chromatography |
| IPA | Isopropyl alcohol |
| LC/MS | Liquid chromatography coupled to mass spectrometry |
| LiHMDS | Lithium hexamethyldisilazide |
| m | multiplet |
| M | Molecular ion |
| mCPBA | 3-Chloroperoxybenzoic acid |
| Me | methyl |
| min | minute |
| MS | Mass spectrometry |
| m/z | Mass-to-charge ratio |
| N | Normal (unit of concentration) |
| NMO | 4-methylmorpholine N-oxide |
| NMR | Nuclear Magnetic Resonance |
| PG | Protecting group |
| PyBOP | Benzotriazole-1-yl-oxy-trispyrrolidinophosphonium hexafluorophosphate |
| RPMI | Roswell Park Memorial Institute series of media |
| q | Quartette (or quartet) |
| Rf | Retention factor |
| Rt | Retention time |
| s | Singlet |
| Tert | Tertiary |
| TFA | Trifluoroacetic acid |
| THAB | Tetrahexylammonium bromide |
| THF | Tetrahydrofuran |
| TLC | Thin Layer Chromatography |
| TRIS | tris(hydroxymethyl)aminomethane |
| TsOH | p-toluenesulfonic acid |
| UV | ultraviolet |
| Vis | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

An illustration of the preparation of compounds of the present invention is shown in the following schemes. Unless otherwise indicated in the schemes, the variables have the same meaning as described above.

The present invention also relates to processes for manufacturing the compounds of Formulae (I), (II), Subformula IA-IH as well as those disclosed in Table 1, according to the hereinafter described schemes and working examples.

Scheme 1

Scheme 1 illustrates the general synthesis route used for the synthesis of all Examples 2.1-2.20 according to the Formula (I). The first step is a condensation reaction between a substituted aniline (11) and 3-fluoro-isonicotinic acid, or derivative thereof (12), to afford the respective acid intermediates (13). The acid intermediates were in turn reacted with suitable amines or alcohols to afford amides or esters (14) respectively. In cases when a protecting group, (e.g. an acetonide group, or other) was present, a suitable de-protection step was included at the end to yield compounds (15).

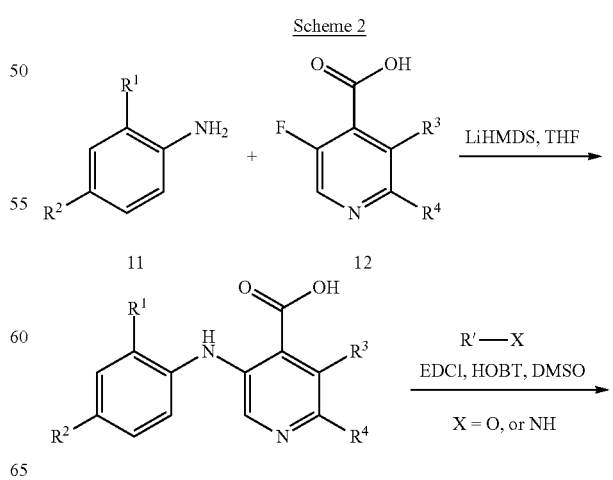

15

-continued

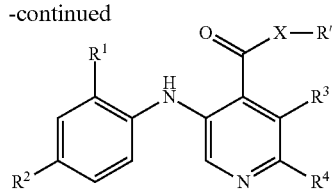

14

↓ deprotection (when necessary)

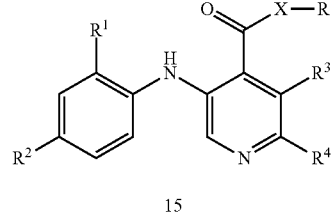

15

16

-continued

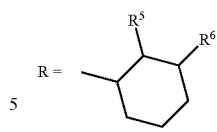

Scheme 2 illustrates the synthesis of a preferred aminediol intermediate, or the diol-protected analog thereof. The synthesis starts from racemic cyclohex-2-enol (16) first with acetylation. The acetyl group of (17) is then substituted in a stereospecific manner in a palladium-catalyzed reaction with potassium phthalimide in the presence of Trost ligand (as described by Trost et al. in *J. Am. Chem. Soc.* 1994, 116, 4089-4090) to afford compound (18). The double bond was then syn-dihydroxylated by treatment with osmium tetroxide to give diol (19), followed by either direct removal of the phthalimido group (to afford amine 27), or by first protection of the diol as an acetonide (20) and then removal of the phthalimido group to afford amine (21).

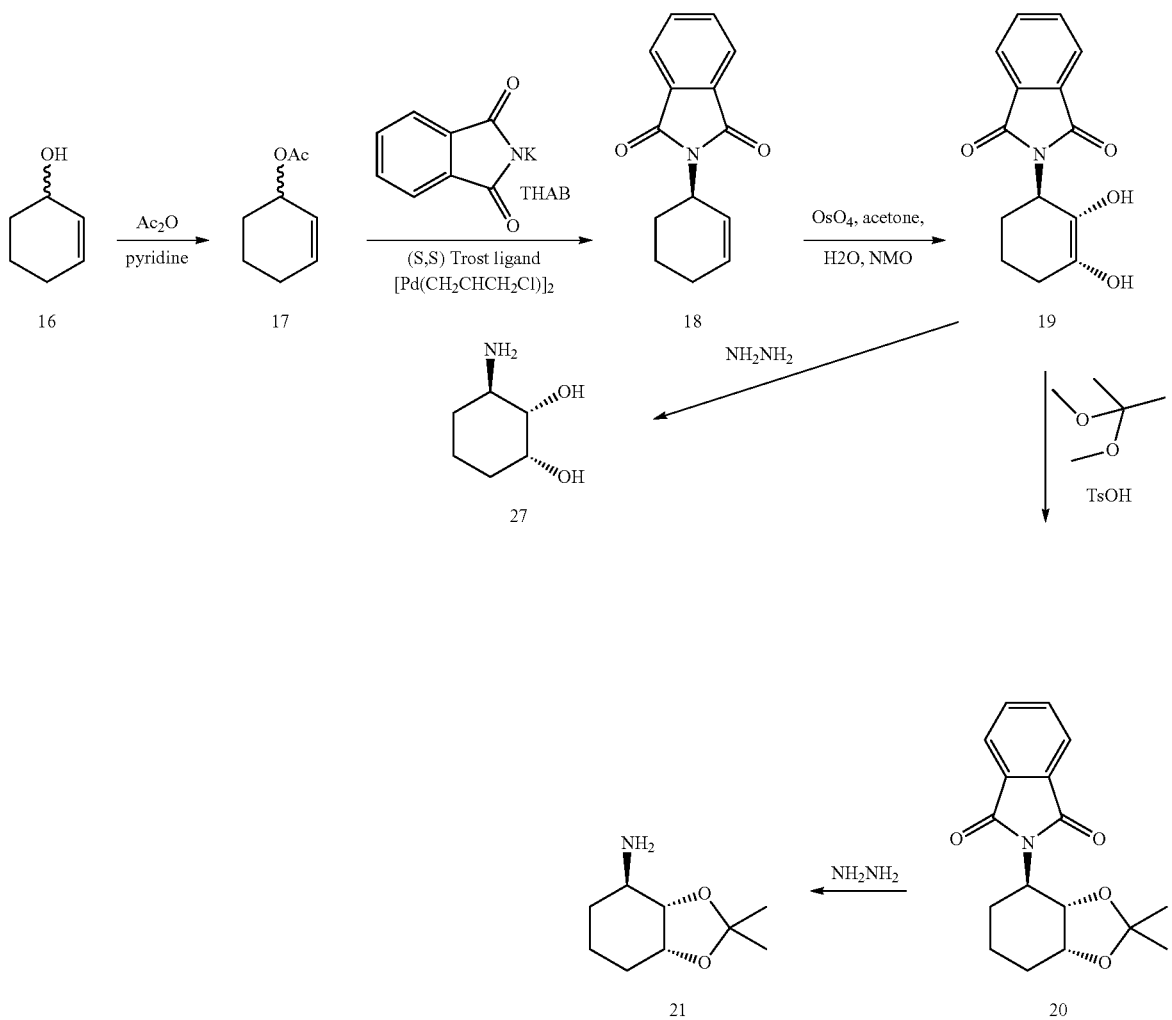

In Scheme 3 the synthesis of racemic aminodiols is illustrated. As described in (1) Nishikawa, N; Asai, M; Ohyabu, N; Isobe, M. *J. Org. Chem.* 1988, 188-192. and (2) Donohoe, J. T.; Blades, K; Moore, P. R.; Waring, M. J.; Winter, J. J. G.; Helliwell, M.; Newcombe, N. J.; Stemp, G. *J. Org. Chem.* 2002, 7946-7956, the synthesis starts with the Overman rearrangement of racemic cyclohex-2-enol (16) (via a trichloracetimidate intermediate) to afford tricholoracetamide (22) which is then syn-dihydroxylated by treatment with osmium tetroxide to give diols 23-26. The resulting diastereomeric mixture of four aminodiols (23-26) is separable by achiral chromatography into two racemic pairs (23/24 and 25/26), which then can be deprotected to the corresponding racemic aminodiols (27/28 and 29/30).

Method details: (I) runs on a Quaternary Pump G1311A (Agilent) with UV/Vis diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B:

A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent

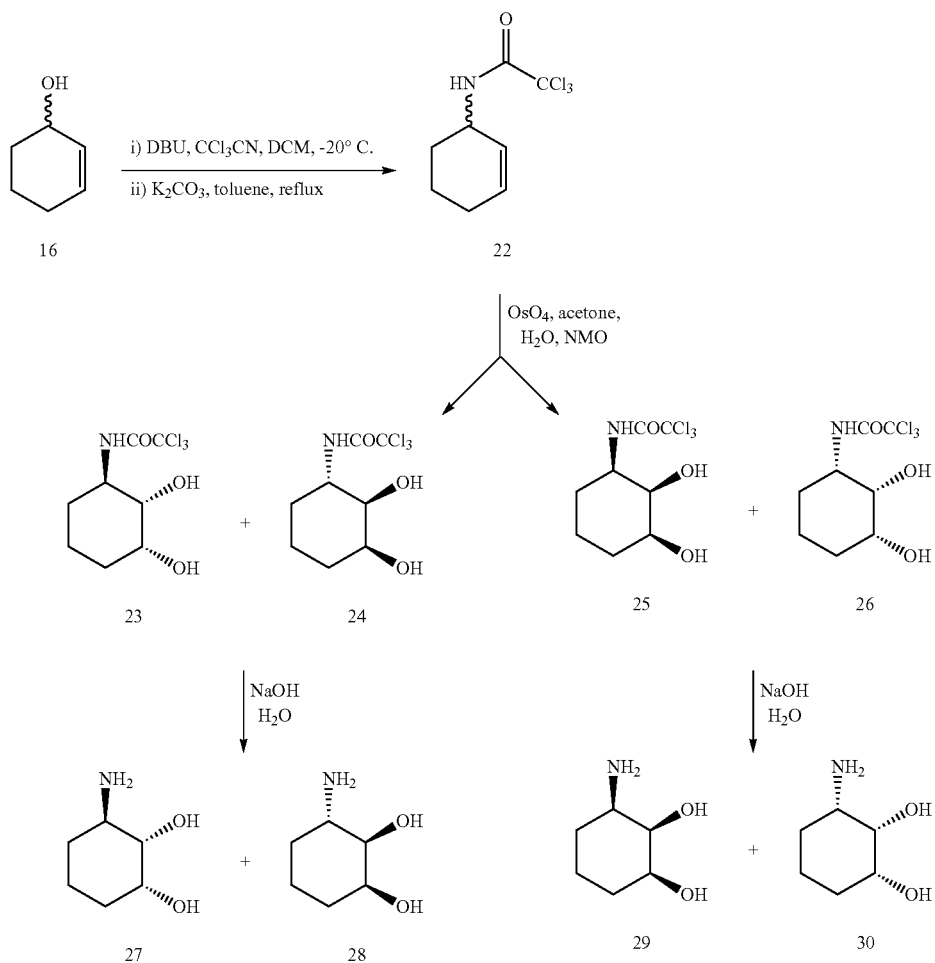

EXAMPLES

The examples presented below are intended to illustrate particular embodiments of the invention, and are not intended to limit the scope of the specification or the claims in any way.

1 Analytics

Analytical LC/MS was Performed Using the Following Two Methods:

Method A:

A Discovery $C^{18}$, 5 μm, 3×30 mm column was used at a flow rate of 400 μl L/min, sample loop 5 μL, mobile phase: (A) water with 0.1% formic acid, mobile phase, (B) methanol with 0.1% formic acid; retention times are given in minutes.

G1956B (SL) MS detector in ESI+mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC

Preparative HPLC was performed using either a Waters Atlantis dC$_{18}$ OBD™ 10 µM (30×250 mm) column or a Waters Sunfire Prep O$_{18}$ OBD 10 µM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

2 Chemical Synthesis 2.1 Cyclohex-2-enyl acetate (17)

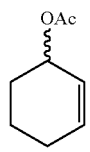

To a solution of 2-cyclohexen-1-ol (16) (45.5 mmol, 5.02 mL) in pyridine (0.27 mol, 22 mL) at 0° C., acetic anhydride was added dropwise and the reaction mixture was stirred at 0° C. for ½ h. The ice bath was removed, and the mixture was stirred at room temperature overnight. The mixture was diluted with EtOAc, washed with HCl (1 N), saturated NaHCO$_3$, brine, and concentrated in vacuo to give 6 g (94%) of the crude product 17 which was used in the next step without further purification. TLC with 20% EtOAc/Hexane, stained with 5% H$_2$SO$_4$/EtOH, Rf for (16): 0.4, Rf for (17): 0.8.

2.2 2-[(1R)-cyclohex-2-en-1-yl]-1H-isoindole-1,3 (2H)-dione (18)

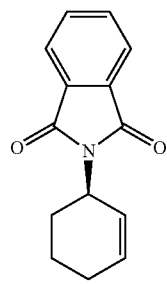 [SMILES: O=C1c2ccccc2C(=O)N1[C@H]1C=CCCC1]

To a mixture of potassium phthalimide (160 mmol, 29.6 g), N,N-(1S,2S)-cyclohexane-1,2-diylbis[2-(diphenylphosphino)benzamide] (Trost ligand) (6 mmol, 4.14 g), [Pd(p-allyl)Cl]$_2$ (2 mmol, 0.73 g) and tetrahexylammonium bromide (216 mmol, 94 g) in anhydrous DCM (40 mL) under N$_2$, 2-cyclohexen-1-yl acetate (17) (13 g crude) in 40 mL of anhydrous DCM was added. The mixture was stirred at ambient temperature overnight. The reaction was then quenched with water (250 mL) and extracted with DCM (3×250 mL). The organics were combined and washed with brine (400 mL), dried over Na$_2$SO$_4$ and concentrated to give the crude product as yellow oil. Recrystallization from MeOH gave 9.024 g of product (purity: 100% by HPLC, 50% yield). The mother liquor was purified by flash chromatography (10% EtOAc/Hexanes) to give 8.8 g of 18 (purity 86% by HPLC, 48% yield). NMR and MS data match published paper: Trost, B. M.; Bunt, R. C. *J. Am. Chem. Soc.* 1994, 4089-4090.

2.3 2-[(1R,2S,3R)-2,3-dihydroxycyclohexyl]-1H-isoindole-1,3(2H)-dione (19)

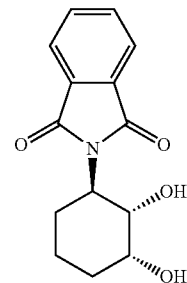

To a suspension of 2-[(1R)-cyclohex-2-en-1-yl]-1H-isoindole-1,3(2H)-dione (18) (19.9 mmol, 4.53 g) and 4-methylmorpholine-N-oxide (60 mmol, 7.01 g) in acetone/water (4:1, 62.5 mL), osmium tetroxide (0.2 mmol, 50 mg) was added. The reaction was stirred for 4 h. The mixture was concentrated and saturated sodium sulfite (40 mL) was added. It was then promptly extracted with EtOAc three times. The combined organic layers were washed with water and brine, dried over MgSO$_4$ and concentrated to give the crude product as a white solid (4.94 g, 95% yield). Chiral HPLC [8.53 min]. Analytical data matched published data (Donohoe, J. T.; et al., *J. Org. Chem.,* 2002, 67, 7946-7956)

2.4 2-[(3aS,4R,7aR)-2,2-dimethylhexahydro-1,3-benzodioxol-4-yl]-1H-isoindole-1,3(2H)-dione (20)

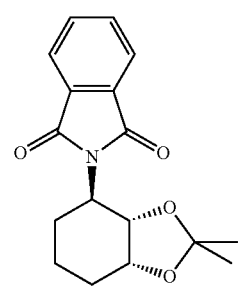 [SMILES: CC1(C)O[C@H]2[C@H](N3C(=O)c4ccccc4C3=O)CCC[C@H]2O1]

To a solution of 2-[(1R,2S,3R)-2,3-dihydroxycyclohexyl]-1H-isoindole-1,3(2H)-dione_(19) (50.0 g, 191.4 mmol) and 2,2-methoxypropane (500 mL, 4.07 mol) in acetone (500 mL), a catalytic amount of p-toluenesulfonic acid was added and the resulting reaction mixture was stirred at room temperature for 3 h. The reaction was quenched with saturated Na$_2$CO$_3$ solution to adjust the pH to 10 and the solvent was removed. Water (750 mL) was added to the residue and extracted with ethyl acetate (2×750, 500 mL). The organics were combined, dried over Na$_2$SO$_4$ and concentrated to give the desired product as a white solid (55.8 g, 96.8% yield). LC/MS [Method B: rt: 6.16 min; m/z: 302 (M+1)].

2.5 (3aS,4R,7aR)-2,2-dimethylhexahydro-1,3-benzodioxol-4-amine (21)

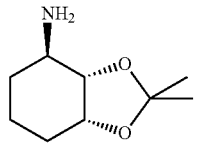

The mixture of 2-[(3aS,4R,7aR)-2,2-dimethylhexahydro-1,3-benzodioxol-4-yl]-1H-isoindole-1,3(2H)-dione (20) (191.4 mmol, 50.00 g), hydrazine (308.4 mmol, 15.0 mL) in ethanol (500 mL) was refluxed for 4 h. The reaction was monitored by HPLC. HPLC analysis showed the reaction did not go to completion (86% conversion). Additional 3 mL of hydrazine was added to the reaction mixture and refluxed for 2 h. The reaction was cooled to 0° C. and filtered. The filter cake was washed with IPA and dried to afford the desired product 21 (9.52 g, 21% yield, purity in weight: 84% based on NMR). The filtrate was concentrated and the residue was taken up in IPA (about 200 mL). The by-product crystallized and was filtered out, and the filtrate was stripped of volatiles and dried to afford a second crop of the desired product 21(28.46 g, 64% yield). TLC (80% MeOH/EtOAc with 1 drop of acetic acid, stained by ninhydrin dip).

2.6 3-[(2-fluoro-4-iodophenyl)amino]isonicotinic acid

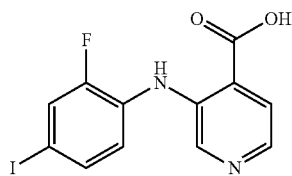 [SMILES: O=C(O)c1ccncc1Nc1ccc(I)cc1F]

A mixture of 2-fluoro-4-iodo-phenylamine (20.0 g, 84.38 mmol) in anhydrous tetrahydrofuran (80 mL) was cooled to −65° C. under an inert atmosphere, prior to slow addition of 1.0 M lithium bis(trimethylsilyl)amide (255 mL, 255 mmol) at a rate that maintained the internal temperature below −55° C. After final addition, the thick slurry was stirred for 30 minutes and then treated with 3-fluoro-isonicotinic acid (8.0 g, 56.69 mmol). The mixture was stirred at room temperature for 4 days and then poured into aqueous 2.0 N sodium hydroxide (1000 mL) and ethyl acetate (250 mL). The layers were separated and the organics were again extracted with aqueous sodium hydroxide (2×1000 mL). The pH of the combined aqueous fractions was adjusted to 2 with concentrated hydrochloric acid, which effected precipitation of a solid. The material was filtered, washed with water (300 mL) and dried under high vacuum at 40° C. for 18 h to afford the product (19.05 g, 53.19 mmol, 94%) as a yellow solid.

2.7 N-[(3aS,4R,7aR)-2,2-dimethylhexahydro-1,3-benzodioxol-4-yl]-3-[(2-fluoro-4-odophenyl)amino]isoicotinamide (31)

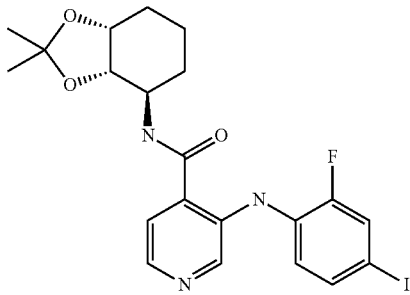 [SMILES: CC1(C)O[C@H]2[C@H](NC(=O)c3ccncc3Nc3ccc(I)cc3F)CCC[C@H]2O1]

A suspension of 3-[(2-fluoro-4-iodophenyl)amino] isonicotinic acid (10.46 g, 29.2 mmol), (3aS,4R,7aR)-2,2-dimethylhexahydro-1,3-benzodioxol-4-amine (21) (5.00 g, 29.2 mmol), 1-hydroxybenzotriazole (4.41 g, 29.2 mmol) and EDCI (5.6 g, 29.2 mmol) in DMF (100 mL) was stirred at room temperature overnight. The reaction was quenched with water (150 mL) and extracted with ethyl acetate (150 mL). Emulsion was formed and collected, filtered and the filtrate was combined to the organic layer. The organic layer was washed with saturated NaHCO$_3$ solution (150 mL) and water (2×150 mL), brine and dried over Na$_2$SO$_4$ and concentrated to give brown foam. The crude was purified by crystallization from IPA. The mother liquor was concentrated and purified by flash chromatography to afford the desired product (12 g. 80% yield). LC/MS [Method A: rt: 7.35 min; m/z: 512 (M+1)].

2.8 (N-[(1R,2S,3R)-2,3-dihydroxycyclohexyl]-3-[(2-fluoro-4-iodophenyl)amino]isonicotinamide) (8)

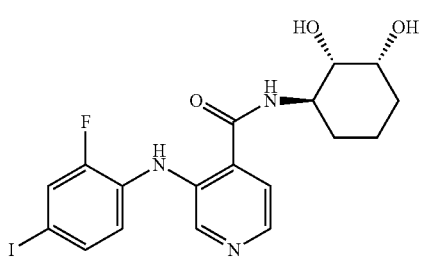 [SMILES: O=C(N[C@@H]1CCC[C@@H](O)[C@H]1O)c1ccncc1Nc1ccc(I)cc1F]

17.62 mL of 2 M HCl in diethyl ether was added to a brown solution of N-[(3aR,4S,7aS)-2,2-dimethylhexahydro-1,3-benzodioxol-4-yl]-3-[(2-fluoro-4-iodophenyl)amino]isonicotinamide (31) (6.65 mmol, 3.15 g) in MeOH (64 mL) and the resulting reaction mixture was stirred at room temperature for 5 h. The reaction mixture was concentrated to about 30 mL and a yellow solid was formed, filtered to give the product as hydrochloride salt. 10 mL of MeOH was added to the salt and ammonium hydroxide was added until pH 10. White solid was formed and solid (1.83 g, 58% yield) was collected by filtration and washed with water. The filtrate was concentrated and second crop was obtained as white solid (0.56 g, 18% yield). LC/MS [Method B: rt: 5.83 min; m/z: 472 (M+1)]. Chiral HPLC [7.06 min].

2.9 2,2,2-Trichloro-N-cyclohex-2-en-1-ylacetamide (22)

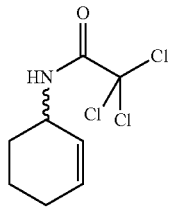 [SMILES: O=C(NC1C=CCCC1)C(Cl)(Cl)Cl]

To a solution of 2-cylohexen-1-ol (16) (18 g, 0.183 mol) in dry dichloromethane (275 ml) DBU (41.88 g, 0.275 mol) was added and the mixture was cooled to −20° C. To this solution, trichloroacetonitrile (47.66 g, 0.330 mol) was added dropwise. The reaction was stirred for 3 h at −20° C. and quenched with aqueous ammonium chloride solution. The organic phase was separated and dried over potassium carbonate. The solvent was removed under vacuum to yield the intermediate cyclohex-2-en-1-yl 2,2,2-trichloroethanimidoate. This was dissolved in toluene (100 ml) and treated with potassium carbonate (30 g). The mixture was refluxed for 12 h. After cooling the mixture was filtered through Celite and the filtrate was evaporated to afford 9 g (20%) of (22) as a solid. LC/MS: Mass found (m/z, MS, 242.9) Method: A—0.1% HCOOH, B—ACN (70%), Flow-0.8 ml/min Column: GENESIS C18 50X4.6 mm 3 U, Rt (min): 1.645: $^1$H NMR (CDCl$_3$, 400 MHz) δ 1.64-1.74 (3H, m), 1.96-2.12 (3H, m), 4.46-4.47 (1H, m), 5.64-5.67 (1H, m), 5.97-5.6.01 (1H, m), 6.59 (1H, bs).

2.10 2,2,2-trichloro-N-[(1RS,2RS,3RS)-2,3-dihydroxycyclohexyl]acetamide (racemic mixture of 23 & 24)

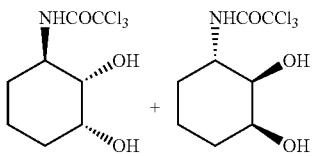

To a solution of 2,2,2-trichloro-N-cyclohex-2-en-1-ylacetamide (22) (4.5 g, 0.0182 mol) and N-methyl morpholine-N-oxide (7.5 g, 0.055 mol) in acetone (100 ml) was added water (25 ml) followed by a catalytic amount of osmium tetroxide (0.1 g, solid). The reaction mixture was stirred at room temperature for 14 h and quenched with saturated solution of sodium sulfite (20 ml). The mixture was stirred for an additional 20 min and then the solvent was removed under vacuum and the residue was purified by chromatography using petroleum ether/ethyl acetate (3/7) as eluent to afford 3.3 g (60%) of the racemic diol as a solid. LC/MS: Mass found (m/z, -MS, 275.8), Method: A—0.1% HCOOH, B—ACN (70%), Flow-0.8 ml/min; Column: GENESIS C18 50X4.6 mm 3 U; Rt (min): 0.695: $^1$H NMR (CDCl$_3$, 400 MHz) δ 1.31-1.70 (6H, m), 3.87-3.92 (2H, m), 4.00-4.10 (1H, m), 7.68 (1H, bs).

2.11 (1RS,2SR,3RS)-3-aminocyclohexane-1,2-diol.HCl (racemic mixture of 27 & 28)

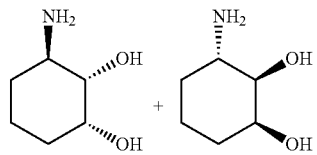 [SMILES: N[C@@H]1CCC[C@@H](O)[C@H]1O ; N[C@H]1CCC[C@H](O)[C@@H]1O]

A mixture of 2,2,2-trichloro-N-[(1RS,2SR,3RS)-2,3-dihydroxycyclohexyl]acetamide (23 & 24) (2.3 g) and 5M aqueous HCl (30 ml) was refluxed for 10 h and evaporated under reduced pressure to afford 1.2 g (86%) of the title compound as viscous liquid. MS: Mass (m/z, MS, 131.9), HPLC>98% Method: A-Water, B—ACN: Flow—0.8 ml/min. Column: C18 XDB, 250×4.6 mm, SC\276. Rt (min), 2.715: $^1$H NMR (CD$_3$OD 400 MHz) δ 1.43-1.91 (6H, m), 2.98-3.02 (1H, m), 3.31-3.42 (1H, m), 3.84 (1H, m).

2.12 N-[(1SR,2RS,3SR)-2,3-dihydroxycyclohexyl]-3-fluoro-5-[(2-fluoro-4-iodophenyl) isonicotinamide (2)

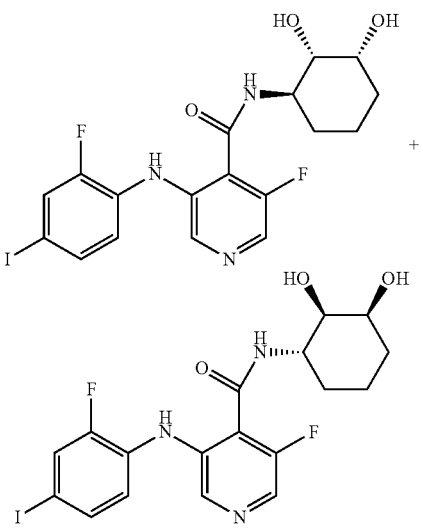

3-Fluoro-5-(2-fluoro-4-iodo-phenylamino)-isonicotinic acid (119 mg, 0.32 mmol) and 1,1'-carbonylbis(1H-imidazole) (67 mg, 0.41 mmol) were suspended in DMSO (2 ml). The mixture was allowed to stir overnight (12 hr) at room temperature. 3-aminocyclohexane-1,2-diol (racemic 27/28) (40 mg, 0.31 mmol) and triethylamine (0.07 ml, 0.49 mmol) were then added. The mixture was stirred for another 6 h at room temperature. Upon completion of the reaction, the reaction mixture was treated with aqueous sodium hydroxide (1 mL, 1.0 M) and stirred at rt for 4 h. The solution was neutralized to pH 7 with conc. HCl. The mixture was then rotavapped to removed most of the water. The resulting mixture was purified by preparative HPLC to afford the product (2). LC/MS [Method A: rt: 4.89 min; m/z: 490 (M+1)].

2.13 N-[(1SR,2RS,3SR)-2,3-dihydroxycyclohexyl]-3-[(2-fluoro-4-iodophenyl)amino]isonicotinamide (3)

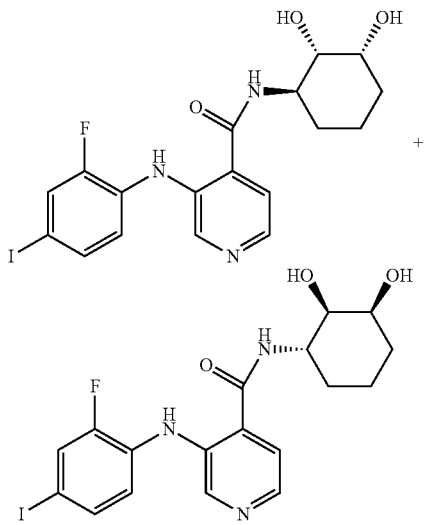

3-(2-Fluoro-4-iodo-phenylamino)-isonicotinic acid (300 mg, 0.84 mmol.) and 1,1'-carbonylbis(1H-imidazole) (177 mg, 1.1 mmol) were suspended in DMSO (4 ml). The mixture was allowed to stir overnight (12 hr) at room temperature. 3-aminocyclohexane-1,2-diol (racemic 27/28) (110 mg, 0.84 mmol) was then added. The mixture was stirred for another 12 h at room temperature. The mixture was separated by preparative HPLC to afford two products, racemic amide (3) and racemic esters (4). LC/MS [Method A: rt: 6.01 min; m/z: 472 (M+1)]. Chiral HPLC [7.10 min, 13.12 min].

2.14 3-Fluoro-5-(2-fluoro-4-iodo-phenylamino)-isonicotinic acid (1RS,2SR,3RS)-3-amino-2-hydroxy-cyclohexyl ester (4)

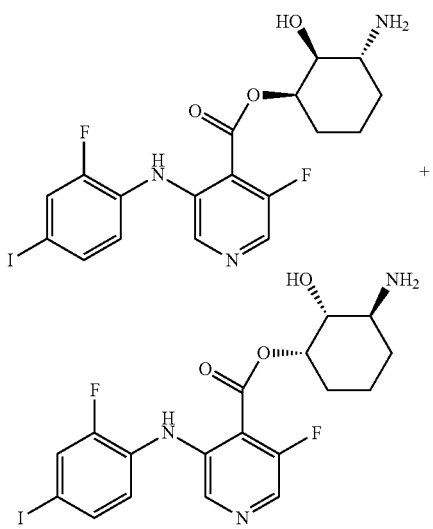

Please see Example 2.13. LC/MS [Method A: rt: 4.53 min; m/z: 472 (M+1)].

2.15 2-Chloro-N-((1RS,2SR,3RS)-2,3-dihydroxy-cyclohexyl)-5-(2-fluoro-4-iodo-phenylamino)-sonicotinamide (1)

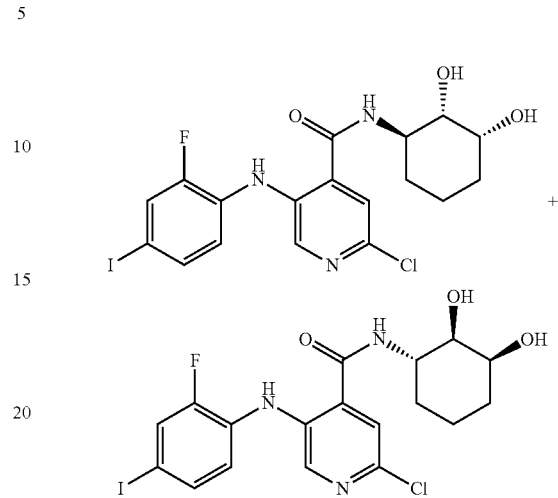

2-Chloro-5-(2-fluoro-4-iodo-phenylamino)-isonicotinic acid (75 mg, 0.19 mmol) and 1,1'-carbonylbis(1H-imidazole) (40 mg, 0.25 mmol) were suspended in DMSO (2.5 ml). The mixture was allowed to stir over night (12 h) at room temperature. 3-aminocyclohexane-1,2-diol (racemic 27/28) (32 mg, 0.19 mmol) and triethylamine (0.05 ml, 0.38 mmol) were then added. The mixture was stirred overnight at room temperature. The mixture was purified by preparative HPLC to afford the product LC/MS [Method B: rt: 5.359 min; m/z: 506 (M+1)].

2.16 3-(4-Bromo-2-fluoro-phenylamino)-N-((1RS,2SR,3RS)-2,3-dihydroxy-cyclohexyl)-isonicotinamide (5)

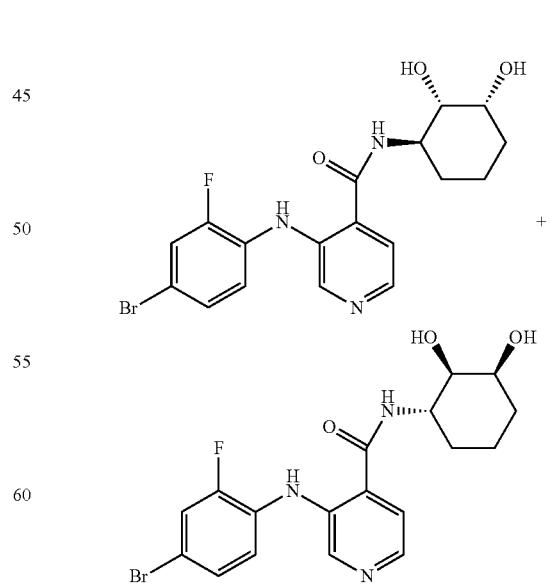

Prepared by the general procedure for (1), LC/MS [Method B: rt: 5.602 min; m/z: 425 (M+1)].

2.17 3-(4-Bromo-2-chloro-phenylamino)-N-((1RS,2SR,3RS)-2,3-dihydroxy-cyclohexyl)-isonicotinamide (6)

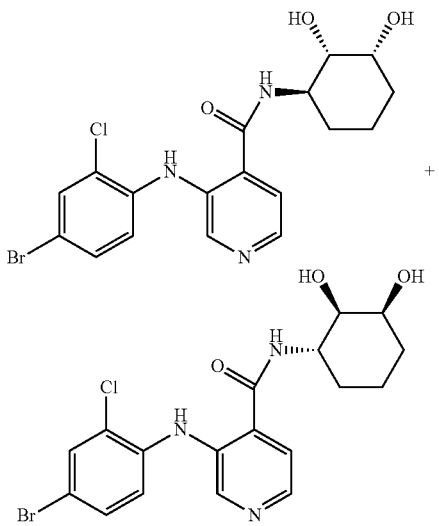

Prepared by the general procedure for (1), LC/MS [Method B: rt: 6.163 min; m/z: 441 (M+1)].

2.18 N-((1R,2S,3R)-2,3-Dihydroxy-cyclohexyl)-3-(2-fluoro-phenylamino)-isonicotinamide (10)

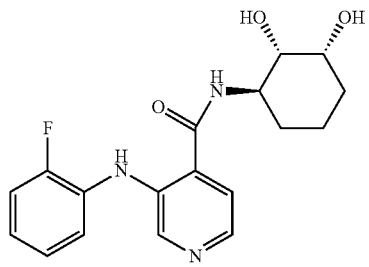 [SMILES: O=C(N[C@@H]1CCC[C@@H](O)[C@H]1O)c1ccncc1Nc1ccccc1F]

A sealed tube was charged with (N-[(1R,2S,3R)-2,3-dihydroxycyclohexyl]-3-[(2-fluoro-4-iodophenyl)amino]isonicotinamide) (8) (42 mg, 0.09 mmol), Sodium borohydride (34 mg, 0.89 mmol), palladium dichloride (7.9 mg, 0.04 mmol), sodium hydroxide (17.8 mg, 0.45 mmol), THF-Water (1:1, 3 ml). The mixture was stirred at room temperature for 2 days. The mixture was filtered and the filtrate was concentrated. The resulting residue was subjected to flash chromatography to obtain the product. LC/MS [Method A: rt: 0.43 min; m/z: 346 (M+1)].

2.19 3-(4-bromo-2-fluorophenylamino)-N-((1R,2S,3R)-2,3-dihydroxycyclohexyl)isonicotinamide (9)

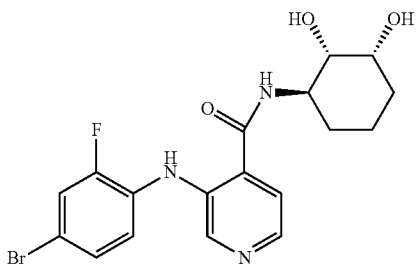 [SMILES: O=C(N[C@@H]1CCC[C@@H](O)[C@H]1O)c1ccncc1Nc1ccc(Br)cc1F]

Prepared by the general procedure for (1) except, instead of a racemic mixture of diols, chirally pure 3-aminocyclohexane-1,2-diol (27) was used. LC/MS [Method B: rt: 5.19 min; m/z: 426.1 (M+1)].

2.20 N-((1S,2R,3S)-2,3-dihydroxycyclohexyl)-3-(2-fluoro-4-iodophenylamino)isonicotinamide (7)

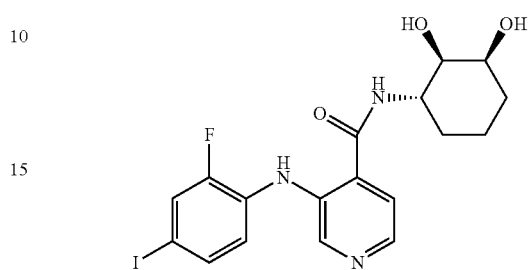

Prepared by the general procedure for (1) except, instead of a racemic mixture of diols, chirally pure 3-aminocyclohexane-1,2-diol (28) was used. LC/MS [Method A: rt: 4.54 min; m/z: 472.3 (M+1)].

3. Biological Activity

3.1 MEK-1 Enzyme Assay (LANCE-HTRF)

The activity of the compounds of the present invention may be determined by the following procedure: Inhibition of human MEK1 kinase activity was monitored with a homogenous, fluorescence based assay. The assay uses time resolved fluorescence resonance energy transfer to probe for phosphorylation of ERK1 by MEK1. The assay is carried out in low volume 96 well microtiterplates. In a total volume of 15 µl, compounds are incubated with 100 nM MEK1, 15 µM ATP, 300 nM ERK2 employing a buffer containing 20 mM TRIS/HCl, 10 mM $MgCl_2$, 100 µM $NaVO_4$, 1 mM DTT, and 0.005% Tween 20 (pH 7.4). After two hours, 5 nM Europium-anti-PY20 (Perkin Elmer) and 50 nM Anti-GST-Allophycocyanin (CisBio) in buffer containing 50 mM EDTA and 0.05% BSA are added and the reaction incubated for one hour in the dark. Time-resolved fluorescence is measured using a LJL-Analyst (Molecular Devices) with an excitation wavelength of 340 nm and an emission wavelength of 665 nm. The final concentration of DMSO is 2%. To assess the inhibitory potential of the compounds, IC50-values were determined, as shown in Table 1.

3.2 Tumor Cell Proliferation Assays (ATP Lite)

Murine colon C26, human melanoma A375 and human pancreatic MiaPaCa-2 cells were plated in 96 well Corning white plates (1500 cells/well for C26, and 2000 cells/well for A375, and MiaPaCa-2) and cultured overnight at 37° C. in 5% $CO_2$. Inhibitors were serially diluted in 100% DMSO and subsequently added to cells to reach a final concentration of 0.25% DMSO. The cells were incubated for 4 days in the presence of test compounds in cell growth media (DMEM with 10% fetal bovine serum, 2 mM glutamine for C26, and MiaPaCa-2, and RPMI with 10% fetal bovine serum, 2 mM glutamine for A375). Cell proliferation was quantitated using the ATP lite cell proliferation kit (Packard). Inhibition of cell proliferation is shown in Table 1. Columns 2-5 show the concentration of compounds required to induce 50% cell death (IC50 in µM) of human endometriotic cells.

TABLE 1

| Compound | MEK1 (IC50, µM) | C26 (IC50, µM) | A375 (IC50, µM) | MIAPACA (IC50, µM) |
|---|---|---|---|---|
| (1) | 0.0345 | 0.002 | 0.002 | 0.002 |
| (2) | 0.074 | 0.005 | 0.001 | 0.0045 |
| (3) | 0.0948 | 0.016 | 0.0014 | 0.0073 |
| (4) | 0.16 | 0.02 | 0.0855 | 0.049 |
| (5) | 0.098 | 0.073 | 0.0075 | 0.0425 |
| (6) | 0.038 | 0.113 | 0.0168 | 0.0753 |
| (7) | 2.67 | 5.4 | 0.274 | 2.12 |
| (8) | 0.133 | 0.0047 | 0.0016 | 0.0027 |
| (9) | not tested | not tested | not tested | not tested |
| (10) | 0.189 | 0.15 | 0.0215 | 0.074 |

3.3 In Vivo Efficacy Studies (Mouse Xenograft Models)

Male nude (nu/nu) mice were injected subcutaneously above the right foreleg with certain number of cells of human tumor cell lines such as Colo-205, A375 or MiaPaCa2. Tumors were measured with calipers one week after cells were implanted. Tumor length (l) and width (w) were measured and tumor volume was calculated with the equation l*w$^2$/2. Animals were sorted into groups so that each group had a mean tumor volume of 150-200 mm$^3$ and treatments with compounds were started (designated as Day 0). Tumor volume and body weight were measured for each animal on Days 0, 4, 6, 8, 10, 12 and 14. Tumor volume and percent body weight were analyzed via Two-Way Repeated Measures Analysis of Variance (RM-ANOVA) followed by Fisher's post-hoc multiple pair-wise comparisons of treatment group means. Compounds in this embodiment were efficacious in these tumor models and resulted in dose-dependent tumor growth inhibition, including tumor regression or tumor. For example compound (9) produced 98.5% tumor growth inhibition in the Colo-205 xenograft model when administered daily at dose 1.5 mg/kg by the oral route. Compound (8), in the same model, produced 100.69% tumor growth inhibition (TGI) when given at 50 µg/kg*day by the oral route, and 115.33% tumor growth inhibition when given at 150 µg/kg/day. In the MiaPaCa2 model, compound (8) gave 100.97% TGI at 33 µg/kg/day, and 110.74% TGI at 50 µg/kg/day.

The invention claimed is:

1. A method of inhibiting MEK activity in a subject suffering from a disease related to the hyperactivity of MEK or a disease modulated by the MEK cascade in mammals, comprising administering to a subject a compound of Formula (I)

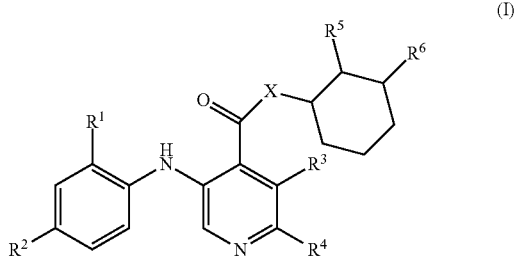

or a pharmaceutically acceptable salt, solvate or prodrug thereof, wherein:
X is NH or O,
R$^1$ is hydrogen, methyl, ethyl, n-propyl, i-propyl, SH or Hal,
R$^2$ is hydrogen, methoxy, ethoxy, acetylene, cyano, SH or Hal,
R$^3$, R$^4$ are independently selected from hydrogen, SH or Hal,
R$^5$, R$^6$ are independently selected from OH, SH or NH$_2$ and
Hal is F, Cl, Br or I.

2. A method of inhibiting MEK activity in a subject suffering from a disease related to the hyperactivity of MEK or a disease modulated by the MEK cascade in mammals, comprising administering to a subject a compound according to claim 1 in which radicals not designated in greater detail have the meaning indicated for the Formula (I) according to claim 1 but in which:
in Subformula IA
X is NH,
R$^1$ is Hal, methyl or ethyl,
R$^2$ is hydrogen, Hal, methoxy or acetylene,
R$^3$ is hydrogen or Hal,
R$^4$ is hydrogen or Hal,
R$^5$, R$^6$ are OH,
Hal is F, Cl, Br or I,
in Subformula IB
X is NH,
R$^1$ is Hal,
R$^2$ is hydrogen or Hal,
R$^3$ is hydrogen or Hal,
R$^4$ is hydrogen or Hal,
R$^5$, R$^6$ are OH,
Hal is F, Cl, Br or I,
in Subformula IC
X is NH,
R$^1$ is F, Cl, methyl or ethyl,
R$^2$ is hydrogen, I, Br, methoxy or acetylene,
R$^3$ is hydrogen or Hal,
R$^4$ is hydrogen or Hal,
R$^5$, R$^6$ are OH,
Hal is F, Cl, Br or I,
in Subformula ID
X is NH,
R$^1$ is F, Cl, methyl or ethyl,
R$^2$ is hydrogen, I, Br, methoxy or acetylene,
R$^3$ is hydrogen or F,
R$^4$ is hydrogen or Cl
R$^5$, R$^6$ are OH,
in Subformula IE
X is NH,
R$^1$ is F or Cl,
R$^2$ is I or Br,
R$^3$ is hydrogen or F,
R$^4$ is hydrogen or Cl
R$^5$, R$^6$ are OH,
in Subformula IF
X is NH,
R$^1$ is F or Cl,
R$^2$ is I or Br,
R$^3$ is hydrogen or F,
R$^4$ is hydrogen or Cl,
R$^5$, R$^6$ are OH,
in Subformula IG
X is NH,
R$^1$ is F or Cl,
R$^2$ is I or Br,
R$^3$ is hydrogen,
R$^4$ is hydrogen,
R$^5$, R$^6$ are OH,
and in Subformula IH
X is NH, $R^1$ is F,
$R^2$ is I,
$R^3$ is hydrogen or F,
$R^4$ is hydrogen or Cl,
$R^5$, $R^6$ are OH,
and pharmaceutically acceptable salts, solvates or prodrugs thereof.

3. A method of inhibiting MEK activity in a subject suffering from a disease related to the hyperactivity of MEK or a disease modulated by the MEK cascade in mammals, comprising administering to a subject the compound of Formula (II):

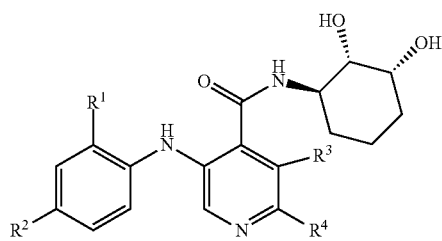
(II)

and pharmaceutically acceptable salts, solvates or prodrugs thereof, wherein $R^1$, $R^2$, $R^3$, and $R^4$ have the meaning indicated for Formula (I) or its subformulae IA, IB, IC, ID, IE, IF, IG or IH.

4. A method of inhibiting MEK activity in a subject suffering from a disease related to the hyperactivity of MEK or a disease modulated by the MEK cascade in mammals, comprising administering to a subject the compound according to Formula (I), wherein, the compound is selected from the group consisting of:

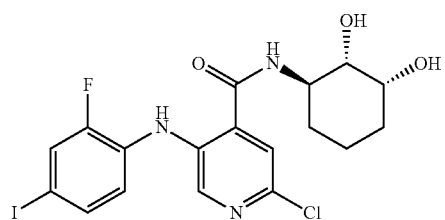
(1)

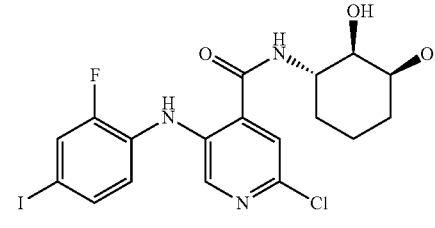
(2)

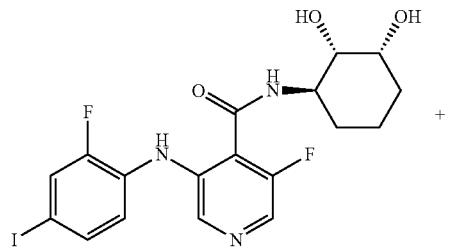

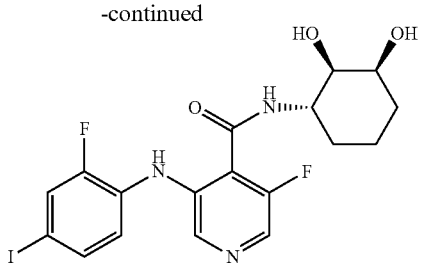

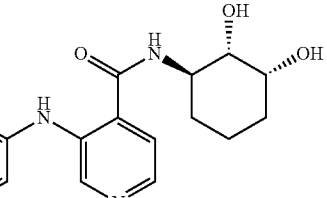
(3)

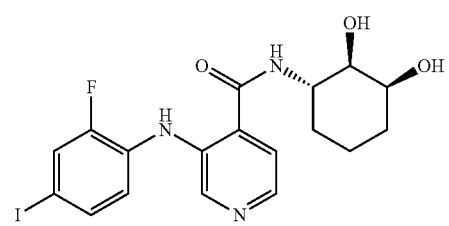

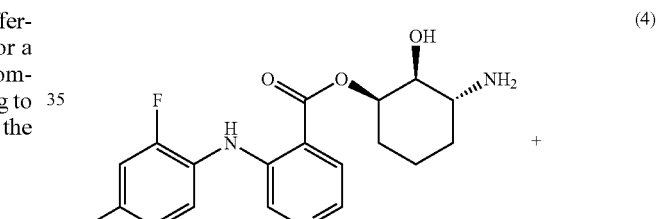
(4)

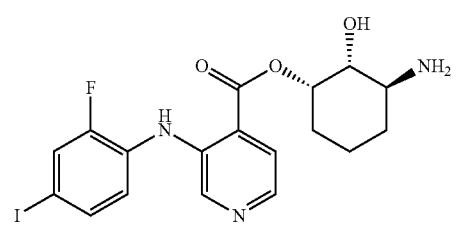

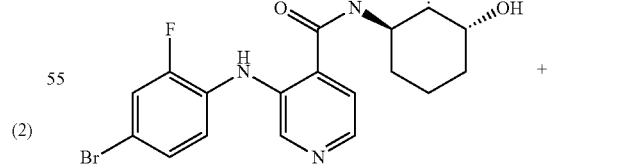
(5)

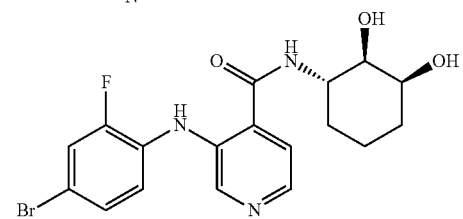

-continued

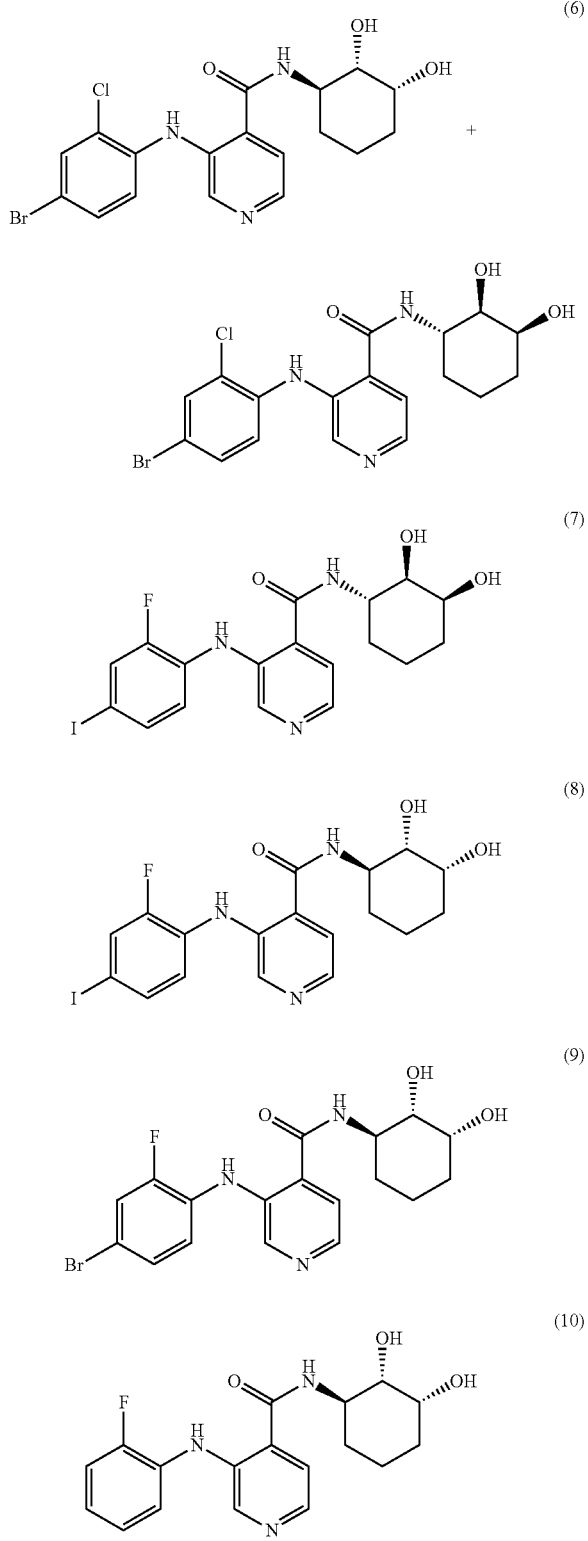

and pharmaceutically acceptable salts, solvates or prodrugs thereof.

5. The method of claim 1, wherein the disease is selected from the group consisting of cancer, inflammation, pancreatitis or kidney disease, pain, benign hyperplasia of the skin, restenosis, prostate, diseases related to vasculogenesis or angiogenesis, tumor angiogenesis, skin diseases selected from psoriasis, eczema, and sclerodema, diabetes, diabetic retinopathy, retinopathy of prematurity, age-related macular degeneration, haemangioma, glioma, melanoma and Kaposi's sarcoma.

6. The method of claim 2, wherein the disease is selected from the group consisting of cancer, inflammation, pancreatitis or kidney disease, pain, benign hyperplasia of the skin, restenosis, prostate, diseases related to vasculogenesis or angiogenesis, tumor angiogenesis, skin diseases selected from psoriasis, eczema, and sclerodema, diabetes, diabetic retinopathy, retinopathy of prematurity, age-related macular degeneration, haemangioma, glioma, melanoma and Kaposi's sarcoma.

7. The method of claim 3, wherein the disease is selected from the group consisting of cancer, inflammation, pancreatitis or kidney disease, pain, benign hyperplasia of the skin, restenosis, prostate, diseases related to vasculogenesis or angiogenesis, tumor angiogenesis, skin diseases selected from psoriasis, eczema, and sclerodema, diabetes, diabetic retinopathy, retinopathy of prematurity, age-related macular degeneration, haemangioma, glioma, melanoma and Kaposi's sarcoma.

8. The method of claim 4, wherein the disease is selected from the group consisting of cancer, inflammation, pancreatitis or kidney disease, pain, benign hyperplasia of the skin, restenosis, prostate, diseases related to vasculogenesis or angiogenesis, tumor angiogenesis, skin diseases selected from psoriasis, eczema, and sclerodema, diabetes, diabetic retinopathy, retinopathy of prematurity, age-related macular degeneration, haemangioma, glioma, melanoma and Kaposi's sarcoma.

9. The method of treating cancer as claimed in claim 5, wherein the cancer is brain, lung, squamous cell, bladder, gastric, pancreatic, breast, head, neck, renal, kidney, ovarian, prostate, colorectal, oesophageal, testicular, gynecological or thyroid cancer, or melanoma, myelogenous leukemia, multiple myeloma, chronic myelogneous leukemia or myeloid cell leukemia.

10. The method of treating cancer as claimed in claim 6, wherein the cancer is brain, lung, squamous cell, bladder, gastric, pancreatic, breast, head, neck, renal, kidney, ovarian, prostate, colorectal, oesophageal, testicular, gynecological or thyroid cancer, or melanoma, myelogenous leukemia, multiple myeloma, chronic myelogneous leukemia or myeloid cell leukemia.

11. The method of treating cancer as claimed in claim 7, wherein the cancer is brain, lung, squamous cell, bladder, gastric, pancreatic, breast, head, neck, renal, kidney, ovarian, prostate, colorectal, oesophageal, testicular, gynecological or thyroid cancer, or melanoma, myelogenous leukemia, multiple myeloma, chronic myelogneous leukemia or myeloid cell leukemia.

12. The method of treating cancer as claimed in claim 8, wherein the cancer is brain, lung, squamous cell, bladder, gastric, pancreatic, breast, head, neck, renal, kidney, ovarian, prostate, colorectal, oesophageal, testicular, gynecological or thyroid cancer, or melanoma, myelogenous leukemia, multiple myeloma, chronic myelogneous leukemia or myeloid cell leukemia.

13. A method for treating cancer selected from the group consisting of colon cancer, melanoma and pancreatic cancer related to the hyperactivity of MEK in mammals, comprising administering to a subject a compound of Formula (I)

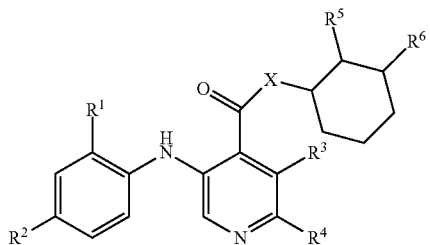

or a pharmaceutically acceptable salt, solvate or prodrug thereof, wherein:
X is NH or O,
$R^1$ is hydrogen, methyl, ethyl, n-propyl, i-propyl, SH or Hal,
$R^2$ is hydrogen, methoxy, ethoxy, acetylene, cyano, SH or Hal,
$R^3$, $R^4$ are independently selected from hydrogen, SH or Hal,
$R^5$, $R^6$ are independently selected from OH, SH or $NH_2$ and Hal is F, Cl, Br or I.

14. A method for treating cancer selected from the group consisting of colon cancer, melanoma and pancreatic cancer related to the hyperactivity of MEK in mammals, comprising administering to a subject a compound according to claim 13 in which radicals not designated in greater detail have the meaning indicated for the Formula (I) according to claim 13 but in which:

in Subformula IA
X is NH,
$R^1$ is Hal, methyl or ethyl,
$R^2$ is hydrogen, Hal, methoxy or acetylene,
$R^3$ is hydrogen or Hal,
$R^4$ is hydrogen or Hal,
$R^5$, $R^6$ are OH,
Hal is F, Cl, Br or I,
in Subformula IB
X is NH,
$R^1$ is Hal,
$R^2$ is hydrogen or Hal,
$R^3$ is hydrogen or Hal,
$R^4$ is hydrogen or Hal,
$R^5$, $R^6$ are OH,
Hal is F, Cl, Br or I,
in Subformula IC
X is NH,
$R^1$ is F, Cl, methyl or ethyl,
$R^2$ is hydrogen, I, Br, methoxy or acetylene,
$R^3$ is hydrogen or Hal,
$R^4$ is hydrogen or Hal,
$R^5$, $R^6$ are OH,
Hal is F, Cl, Br or I,
in Subformula ID
X is NH,
$R^1$ is F, Cl, methyl or ethyl,
$R^2$ is hydrogen, I, Br, methoxy or acetylene,
$R^3$ is hydrogen or F,
$R^4$ is hydrogen or Cl
$R^5$, $R^6$ are OH,
in Subformula IE
X is NH,
$R^1$ is F or Cl,
$R^2$ is I or Br,
$R^3$ is hydrogen or F,
$R^4$ is hydrogen or Cl
$R^5$, $R^6$ are OH,
in Subformula IF
X is NH,
$R^1$ is F or Cl,
$R^2$ is I or Br,
$R^3$ is hydrogen or F,
$R^4$ is hydrogen or Cl,
$R^5$, $R^6$ are OH,
in Subformula IG
X is NH,
$R^1$ is F or Cl,
$R^2$ is I or Br,
$R^3$ is hydrogen,
$R^4$ is hydrogen,
$R^5$, $R^6$ are OH,
and in Subformula IH
X is NH,
$R^1$ is F,
$R^2$ is I,
$R^3$ is hydrogen or F,
$R^4$ is hydrogen or Cl,
$R^5$, $R^6$ are OH,
and pharmaceutically acceptable salts, solvates or prodrugs thereof.

* * * * *